United States Patent
Arand et al.

(10) Patent No.: US 10,493,210 B2
(45) Date of Patent: Dec. 3, 2019

(54) NEGATIVE PRESSURE SYRINGE FOR DRIP PREVENTION

(71) Applicant: Inter-Med, Inc., Racine, WI (US)

(72) Inventors: Brett Arand, Milwaukee, WI (US); John Baeten, Muskego, WI (US); Gary Pond, Milwaukee, WI (US)

(73) Assignee: INTER-MED, INC., Racine, WI (US)

( * ) Notice: Subject to any disclaimer, the term of this patent is extended or adjusted under 35 U.S.C. 154(b) by 54 days.

(21) Appl. No.: 15/384,797

(22) Filed: Dec. 20, 2016

(65) Prior Publication Data

US 2018/0169344 A1 Jun. 21, 2018

(51) Int. Cl.
*A61M 5/315* (2006.01)
*A61M 5/31* (2006.01)

(52) U.S. Cl.
CPC ...... *A61M 5/31513* (2013.01); *A61M 5/3158* (2013.01); *A61M 5/31515* (2013.01); *A61M 2005/3103* (2013.01)

(58) Field of Classification Search
CPC ...... A61M 2005/3103; A61M 5/31511; A61M 5/31513; A61M 5/31515
See application file for complete search history.

(56) References Cited

U.S. PATENT DOCUMENTS

| 4,678,107 A | 7/1987 | Ennis, III |
| 4,708,270 A | 11/1987 | Ruesch |
| 6,796,217 B2 | 9/2004 | Horita et al. |
| 2013/0012888 A1 * | 1/2013 | Okihara ............ A61M 5/31515 604/220 |

OTHER PUBLICATIONS

Spencer, H.R. et al., "Review: The use of sodium hypochlorite in endodontics—potential complications and their management," British Dental Journal, vol. 202, No. 9, May 12, 2007, pp. 555-559.
Ingram, T.A., "Response of the Human Eye to Accidental Exposure to Sodium Hypochlorite," J. Endod 1990; 16:235-237.
Gatot, A. et al., "Effects of Sodium Hypochlorite on Soft Tissues after Its Inadvertent Injection beyond the Root Apex", J. Endod 1991; 17:573-574.
Gopikrishna, V. et al., "An in vivo assessment of the influence of needle gauges on endodontic irrigation flow rate." J. Conserv Dent. Mar.-Apr. 2016; 19(2):189-193.
Park, E. et al., "Apical Pressure and Extent of Irrigant Flow Beyond the Needle Tip during Positive-pressure Irrigation in an In Vitro Root Canal Model," J. Endod Apr. 2013; 39(4):511-515.

* cited by examiner

*Primary Examiner* — Emily L Schmidt
(74) *Attorney, Agent, or Firm* — Brinks Gilson & Lione; Ryan L. Marshall; Jonathan Hartley

(57) ABSTRACT

In the present invention, a dripless syringe is provided that includes a barrel having fluid therein, the barrel defining an open end and a nozzle opposite the open end, a plunger disposed at least partially within the open end and including a body and a push pin extending from one end of the body, a seal plate slidably mounted to the push pin and a bung disposed over the seal plate and the push pin and sealingly engaged between the seal plate and the barrel the seal plate enables the bung to remain in sealing engagement with the interior of the barrel while the plunger is moved within the barrel. Further, when pressure is removed to cease dispensing of the fluid, the pin allows the bung to retract and provide a negative pressure on the fluid to prevent drips of fluid from leaking out of the nozzle.

15 Claims, 11 Drawing Sheets

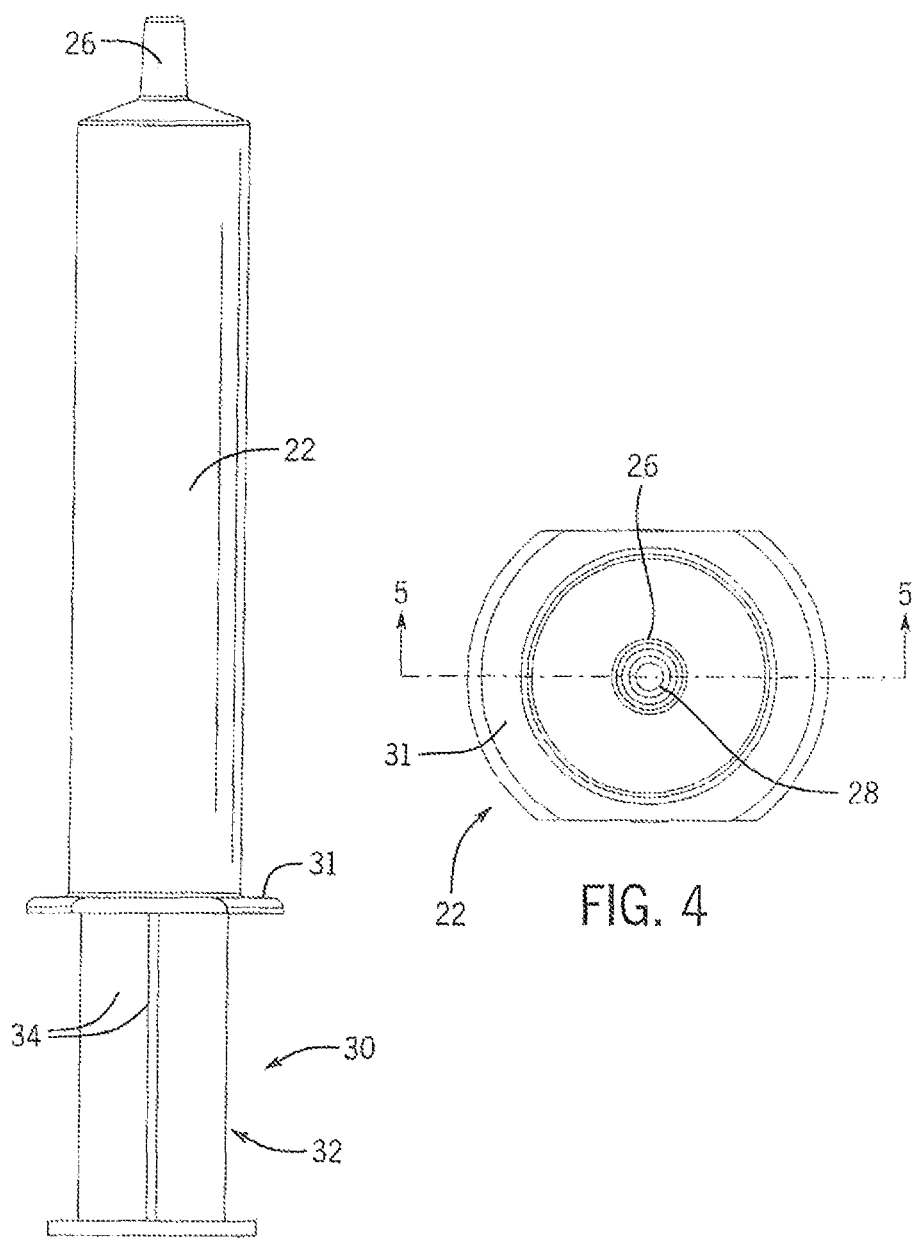

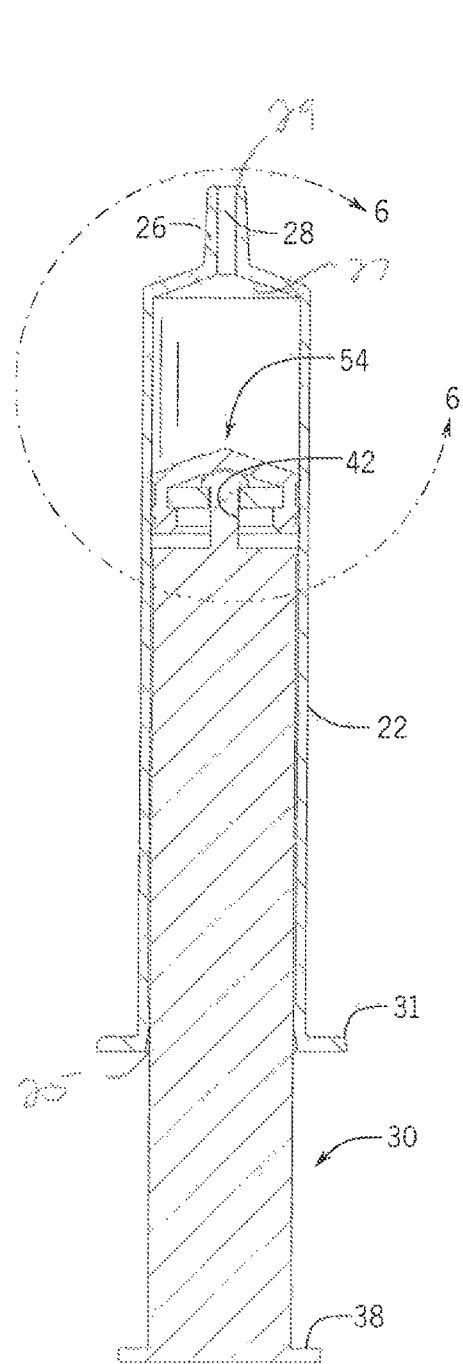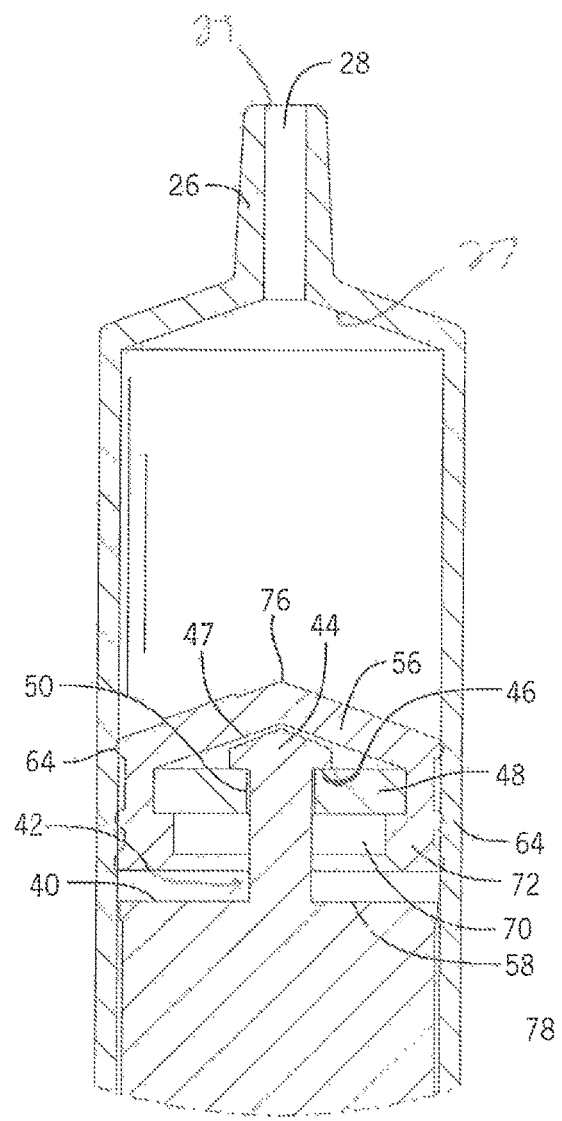
FIG. 5
FIG. 6

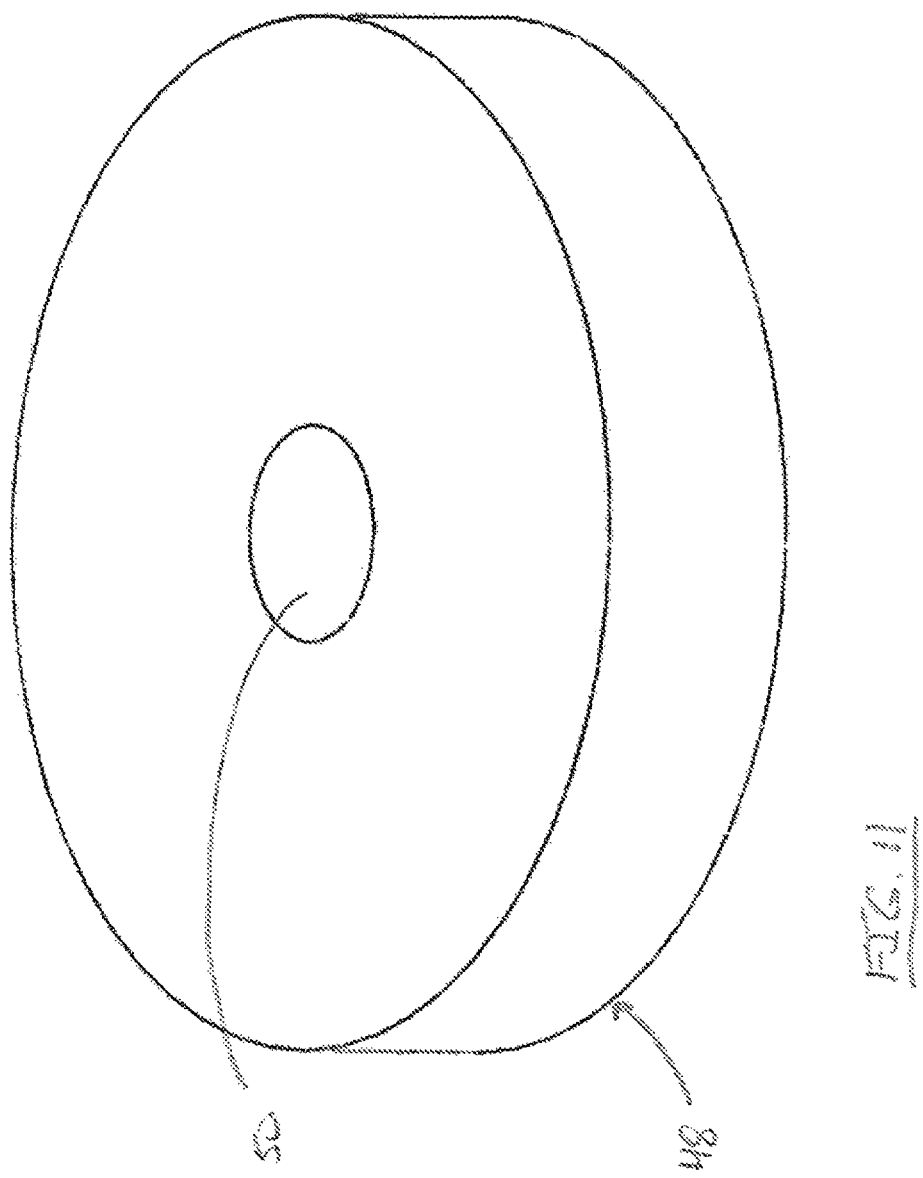

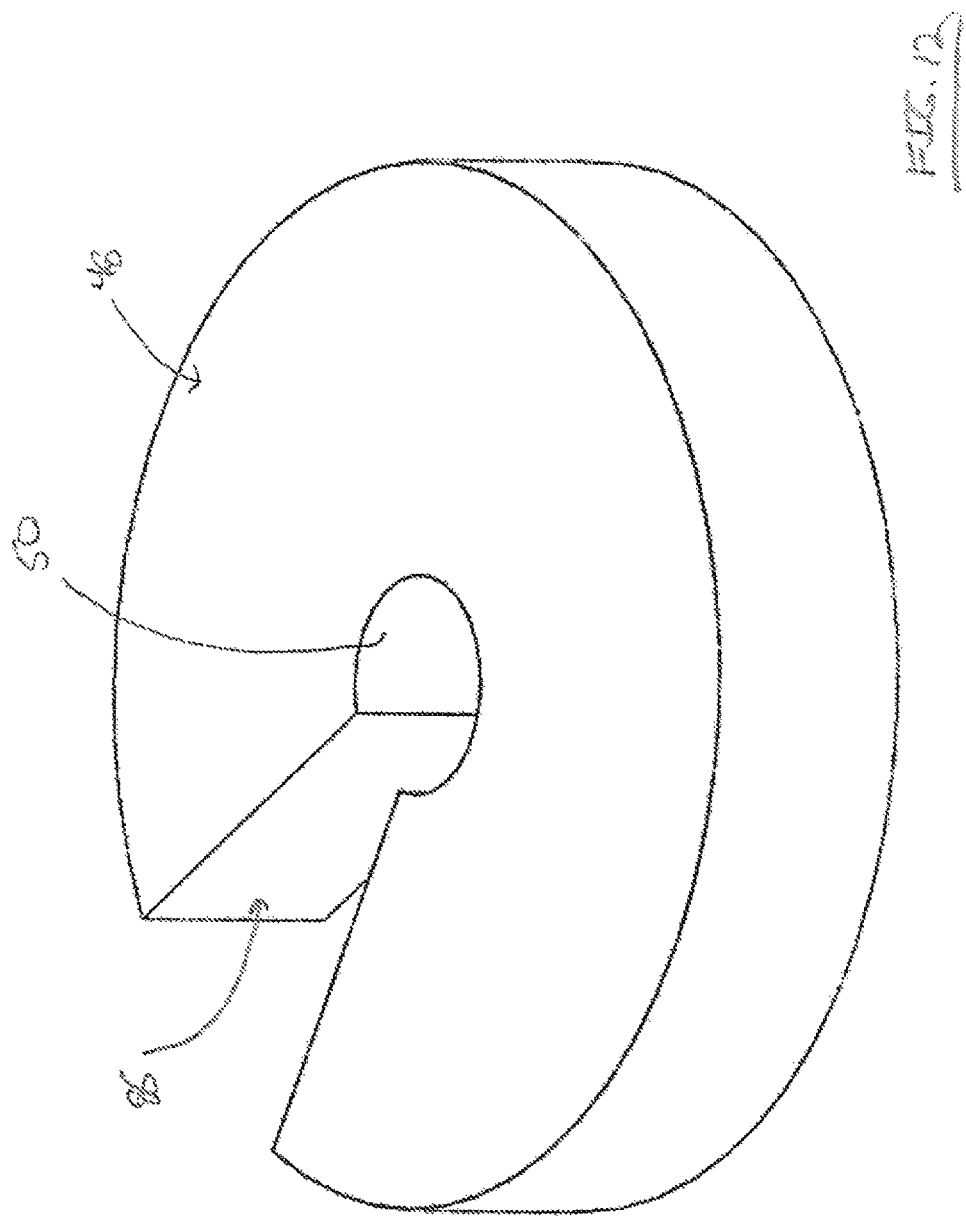

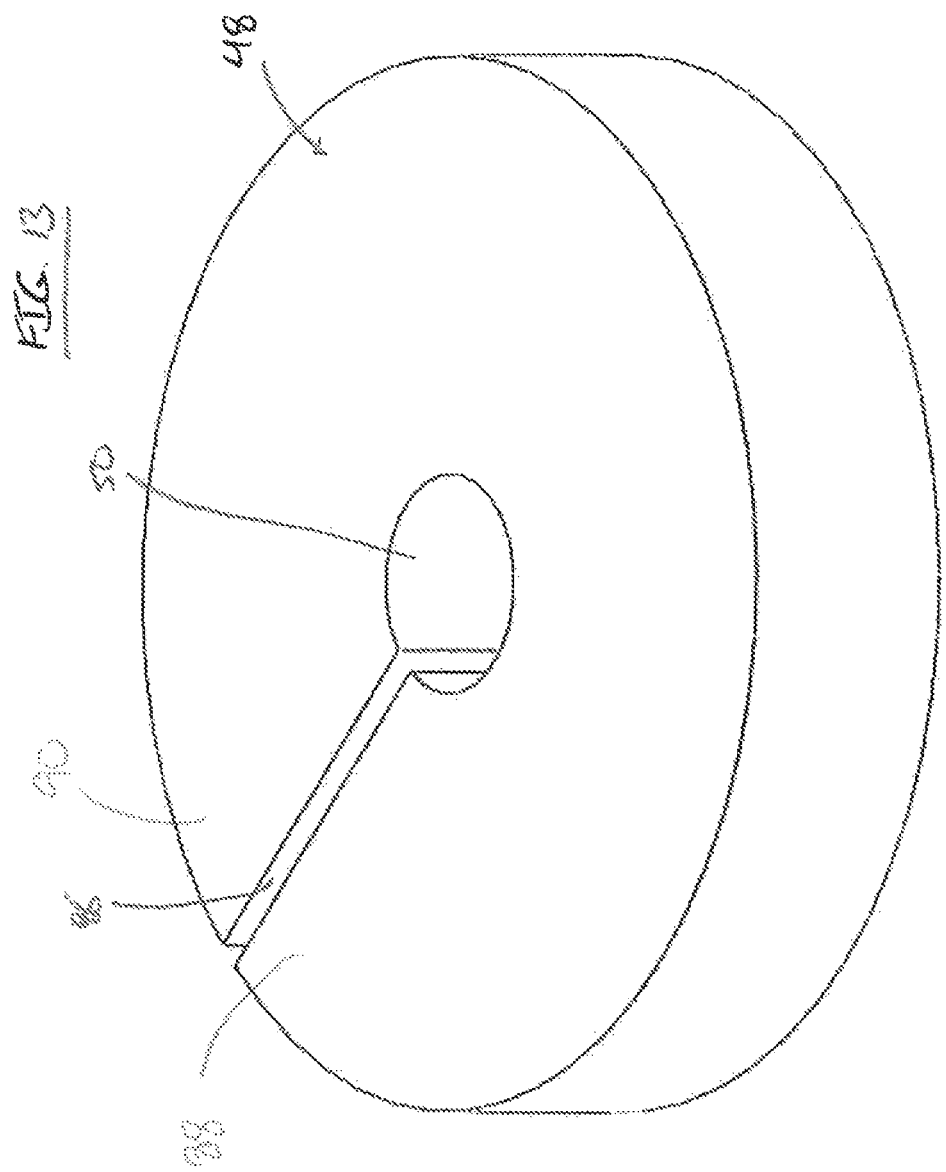

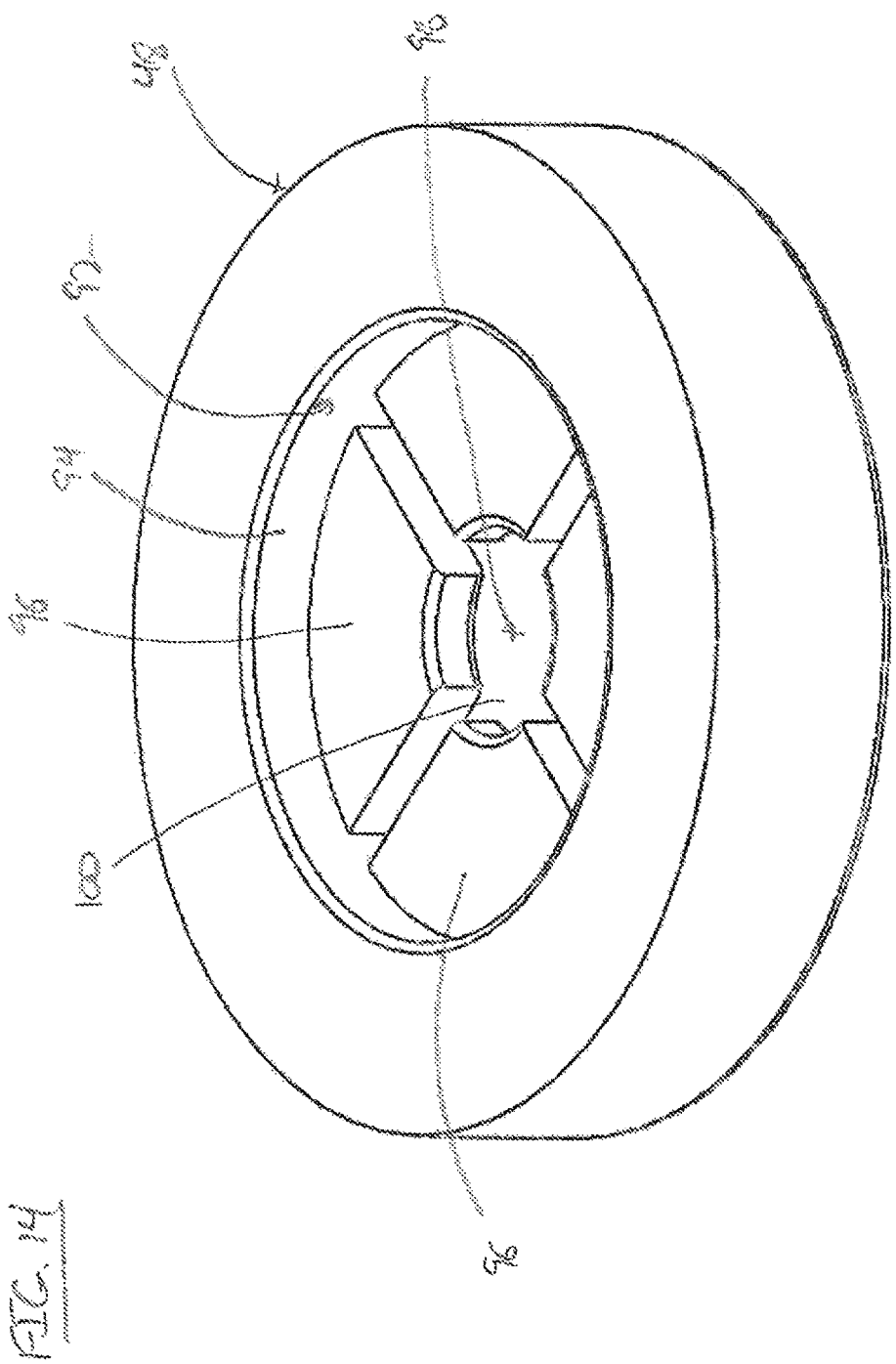

NEGATIVE PRESSURE SYRINGE FOR DRIP PREVENTION

BACKGROUND OF INVENTION

The invention relates generally to syringes and more specifically to pre-tipped syringes utilized to dispense an amount of fluid to a surface.

In various types of medical and dental procedures it is often necessary for an individual to dispense an amount of a fluid onto a surface being treated. The fluids can have various purposes, such as to sterilize, anesthetize, etch, bond, clean or treat in some manner the surface being examined during the procedure.

In order to precisely deliver the fluids onto the surface for the desired purpose, a number of different delivery systems have been developed. One such delivery system is a syringe and application tip. The syringe is formed with a barrel containing an amount of the fluid to be dispensed and a nozzle at one end of the barrel from which the fluid is expelled from the barrel, most commonly the nozzle is a standard luer taper to accept luer tapered application tips. Opposite the nozzle, a plunger is slidably positioned within the barrel and includes a bung that contacts the fluid within the barrel. The plunger can be moved within the barrel in order to compress the fluid via the bung to urge or force the fluid from within the barrel out of the syringe through the nozzle and subsequently through the application tip. The amount of fluid dispensed from the nozzle is controlled by the force applied to the fluid via the plunger and the back pressure developed due to the application tip constrictor diameter, and thus the individual can determine the amount of fluid to be dispensed or the rate at which the fluid is dispensed.

However, with syringes of this type, one significant issue is the inability to immediately stop fluid being dispensed from the syringe once positive pressure has been removed from a user. More specifically, when the pressure being applied to the fluid via the plunger is removed, residual pressure remaining in the fluid within the barrel causes an amount of the fluid to be dispensed, or to drip from the nozzle and/or application tip, even when no pressure is actively being applied to the fluid. As the inadvertent dispensing of the fluid can have highly undesirable consequences, depending on the nature of the fluid and/or the cost of the fluid, among other issues, it is highly desirable to prevent any dripping of the fluid from the syringe. One example of accidental spillage or dripping common to dentistry is the inadvertent spillage of sodium hypochlorite during endodontic procedures. Accidental spillage of sodium hypochlorite is probably the most common accident to occur during root canal irrigation. Even spillage of minute quantities of this agent on clothing will lead to rapid, irreparable bleaching. The patient should wear protective coverings and eyewear, and the practitioner should exercise care when transferring syringes filled with hypochlorite to the oral cavity. Additionally, seemingly mild burns with an alkali such as sodium hypochlorite can result in significant eye injury as the alkali reacts with the lipid in the corneal epithelial cells, forming a soap bubble that penetrates the corneal stroma. The alkali moves rapidly to the anterior eye chamber, making repair difficult. Further degeneration of the tissues within the anterior eye chamber results in perforation, with endophthalmitis and subsequent loss of the eye [Spencer H R, Ike V, Brennan P A. Review: the use of sodium hypochlorite in endodontics—potential complications and their management. Br Dent J. 2007 May 12; 202(9):555-559.].

Ingram recorded a case of accidental spillage of 5.25% sodium hypochlorite into a patient's eye during endodontic therapy [Ingram T A. Response of the human to accidental exposure to sodium hypochlorite. *J Endod* 1990; 16: 235-237]. The immediate symptoms included instant severe pain and intense burning, profuse watering (epiphora) and erythema. Loss of epithelial cells in the outer corneal layer may occur. There may be blurring of vision and patchy colouration of the cornea [Gatot A. Arbelle J. Leiberman A et al. *Effects of Sodium hypochlorite on soft tissues after its inadvertent injection beyond the root apex. J Endod* 1991: 17: 573-574]. Immediate ocular irrigation with a large amount of water or sterile saline is required followed by an urgent referral to an ophthalmologist. Similar complications can occur when sodium hypochlorite accidental drippage or spillage occurs to skin or oral tissues during root canal therapy. As such, an anti-drip syringe and application tip system would be highly advantageous for dental and medical procedures to prevent accidents and patient harm.

In certain prior art solutions to this issue, a number of different types of syringes have been developed in an attempt to counteract latent pressure within the device. One such syringe is disclosed in U.S. Pat. No. 4,678,107, entitled Dripless Dispenser For Liquid And Viscous Fluids, which is expressly incorporated herein by reference for all purposes. In this syringe, a cap having a concave surface is disposed on the end of the plunger disposed within the barrel of the syringe. The concave surface is flattened by a plate on the end of the plunger when pressure is applied to the fluid via the plunger to dispense fluid from the syringe. When the force exerted on the plunger is removed, thereby disengaging the plate from the cap, the cap returns to its concave shape to apply a negative pressure or vacuum on the fluid within the barrel and nozzle, thereby preventing the fluid from dripping out of the nozzle.

However, while the cap includes a pair of sealing rings engaging the cap with the interior surface of the barrel to provide a fluid seal between the cap and the barrel, when the cap is in the concave position there is no support provided to the cap at the sealing rings. Thus, due to the inherent flexibility of the material forming the cap and sealing rings, the sealing rings can become separated from the interior surface of the barrel when the plunger is not actively being pressed against the cap. As a result, the fluid held within the barrel can leak around the cap and out of the barrel around the plunger, which is highly undesirable. As such, the syringe and bung design disclosed in U.S. Pat. No. 4,678,107 would have limited applications for use (i.e. viscous fluids and/or low positive pressures/exertion forces) in order to prevent leakage around the bung during use. In addition to the syringe disclosed in the '107 patent, other prior art dripless syringe designs, such as those disclosed in U.S. Pat. Nos. 4,708,270 and 6,796,217, also include caps or bungs that can deform within the barrel in a manner that comprises the fluid seal between the cap or bung and the barrel.

Endodontic therapy, by virtue of the root canal geometry, requires small gauge needle tips during irrigation. Unfortunately, as described by Gopikrishna et al., needle gauge lumen diameter has a negative impact on therapeutic irrigant flow rates [Gopikrishna V, Sibi S, Archana D, Pradeep Kumar A R, Narayanan L. An in vivo assessment of the influence of needle gauges on endodontic irrigation flow rate. J Conserv Dent. 2016 March-April; 19(2):189-193]. In order to reach optimal flow rates that produce safe apical pressure and fluid exchange beyond the end of the needle tip, considerable pressures are required on the plunger to compensate for smaller needle gauge diameters [Park E, Shen Y, Khakpour M, Haapasalo M. Apical pressure and extent of irrigant flow beyond the needle tip during positive-pressure irrigation in an in vitro root canal model. J Endod. 2013 April; 39(4):511-515.]. Increased forces on the syringe plunger results in increased pressures within the container leading to subsequent spillage/drippage after applied force due to further expansions of the container materials and residual pressures. Syringes designed to overcome this issue thereby need to maintain a fluid tight seal between the bung and barrel under this greater pressure.

Accordingly, it is desirable to develop a syringe capable of preventing dripping of the fluid from the syringe while also maintaining the fluid seal between the plunger and the barrel.

BRIEF DESCRIPTION OF THE INVENTION

There is a need or desire for a dripless syringe that functions to dispense a fluid from the syringe without subsequent dripping of the fluid and that maintains the integrity of the fluid seal between the plunger and the barrel of the syringe at all times.

According to one exemplary non-limiting aspect of the invention, the syringe includes a barrel that includes an open end surrounded by a gripping flange and a dispensing nozzle located opposite the open end. The nozzle tapers from the barrel to a dispensing end through which a fluid can be dispensed from the barrel. The syringe further includes a plunger that is slidably positioned within the barrel. The plunger includes a push plate at one end and a bung disposed on the plunger opposite the push plate. The bung is formed of a resilient material and includes a first section formed to be complementary in shape to the cross-section of the barrel, and a second section extending outwardly from the first portion. The first section defines an interior within which a seal plate is disposed. The seal plate is formed of a rigid material and has a shape complementary to the shape of the interior of the first section in order to enable the seal plate to provide support to the interior of the first section. The seal plate includes a central aperture through which extends a push pin. The pin is affixed at one end to the body of the plunger and enables the seal plate to move or slide along the push pin. Opposite the plunger, the push pin engages the second section of the bung and separates the bung from the plunger, creating an offset between the plunger and the first section of the bung.

In operation, when pressure is initially applied to the plunger, the push pin flexes the second section of the bung outwardly. The bung is made of a material that is compliant and conforms to the inner diameter of the syringe barrel. However, when pressure is applied the material is deformable to take the shape of an applied member but the deformation does not remain permanent once the force is removed. The material is also compatible with common dental materials such as NaOCl, EtOH, EDTA, etchants, hemostatic agents, etc. Suitable materials for the bung include but are not limited to fluoroelastomers (Viton), Buna N (Nitril), PTFE (Teflon), Silicone, and EDPM. Simultaneously, the seal plate slides along the push pin to a position where the offset is removed and the first section of the bung is disposed in contact with the body of the plunger. While the seal plate slides along the push pin, the seal plate holds the first section of the bung against the interior surface of the barrel as the first section slides along the barrel to maintain the fluid seal between the plunger and the barrel. The seal plate generally is sized to fit snuggly within the bung, but can also be oversized or undersized to modify the drag or resistive force between the bung and syringe barrel. This helps to facilitate the distal deformation of the bung which in turn creates the negative internal pressure once external pressure is relived, while maintaining the seal between the bung and syringe barrel. The seal plate can also be oversized or undersized to modify the fluid seal between the bung and syringe barrel.

When pressure on the plunger is released, the drag force and the elastic nature of the material forming the bung causes the second portion to return to the undeformed or unflexed configuration, creating negative pressure in the barrel that acts on the fluid and prevents any drips of fluid from exiting the nozzle. Simultaneously, the push pin is urged towards the seal plate, such that the seal plate moves along the push pin, recreating the offset between the first portion of the bung and the body of the plunger. While the seal plate moves along the push pin, the plate maintains the first portion of the bung in sealing engagement with the interior of the barrel, thereby maintaining the fluid seal between the bung and barrel.

According to one exemplary non-limiting embodiment of the invention, a dripless syringe includes a barrel adapted to receive an amount of fluid therein, the barrel defining an open end and a nozzle opposite the open end, a plunger disposed at least partially within the open end and including a body and a push pin extending from one end of the body, a seal plate slidably mounted to the push pin and a bung disposed over the seal plate and the push pin and sealingly engaged between the seal plate and the barrel.

According to another exemplary non-limiting embodiment of the invention, a plunger for use with a barrel for forming a dripless syringe includes a body, a push pin disposed at one end of the body and a seal plate slidably mounted to the push pin.

According to still a further aspect of one exemplary non-limiting embodiment of the invention, a method of dispensing a fluid from a syringe includes the steps of providing a syringe comprising a barrel including an amount of fluid therein, the barrel defining an open end and a nozzle opposite the open end, a plunger disposed at least partially within the open end and including a body and a push pin extending from one end of the body, a seal plate slidably mounted to the push pin and a bung disposed over the seal plate and the push pin, the bung contacting the fluid and sealingly engaged between the seal plate and the barrel, applying a force to the plunger to press the push pin through the seal plate and against the bung to dispense the fluid from the nozzle and removing the force on the plunger to cease dispensing the fluid from the nozzle.

Other embodiments of the invention that function on the same principle are also possible. The standard bung has a convex cone geometry, but it may also be created with a flat or concave geometry that also deforms and returns to the original shape. Another embodiment employs an insert into the barrel of a solid compressible disk or balloon filled with a compressible gas or fluid. This disk or balloon will compress when the plunger is depressed, and then return to its original size and push the plunger back when pressure on the plunger is released. The disk or balloon must be specified in a way that it is able to push the plunger back to relieve pressure in the fluid without instead expelling more fluid. Another possible embodiment is to have a physical retraction action on the plunger external to the fluid area without the need of a deformable bung, disk or balloon. The plunger and barrel can have a ratcheting or spring action so that when pressure on the plunger is ceased, it is retracted backwards creating negative pressure in the fluid area.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings:

FIG. 3 is side elevational view of the syringe of FIG. 1.

FIG. 4 is top plan view of the syringe of FIG. 1.

FIG. 5 is cross-sectional view along line 5-5 of FIG. 4.

FIG. 6 is circular cross-sectional view along line 6-6 of FIG. 5.

FIG. 11 is an isometric view of one exemplary embodiment of a seal ring according to the invention.

FIG. 12 is an isometric view of another exemplary embodiment of a seal ring according to the invention.

FIG. 13 is an isometric view of still another exemplary embodiment of a seal ring according to the invention.

FIG. 14 is an isometric view of still a further exemplary embodiment of a seal ring according to the invention.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
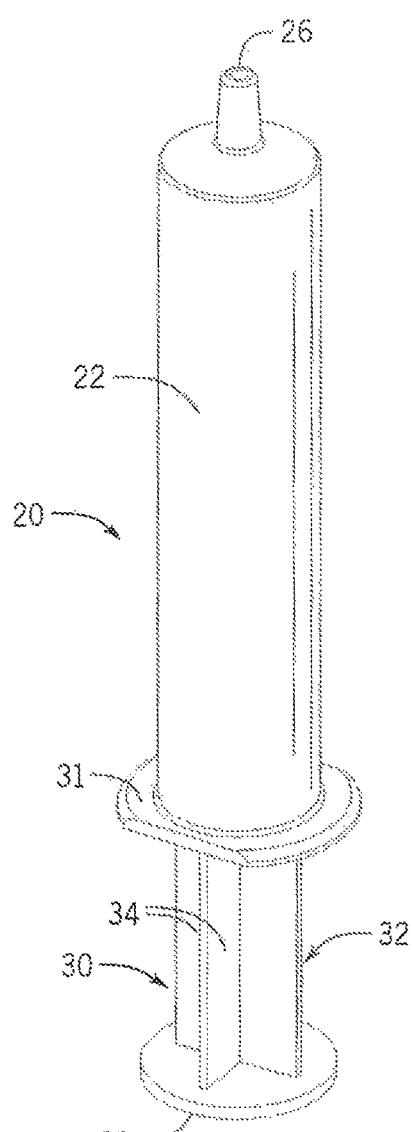
FIG. 1 is an isometric view of a dripless syringe according to one exemplary non-limiting embodiment of the invention.

Referring to FIG. 1, in the illustrated exemplary non-limiting embodiment a syringe or syringe-like device generally designated as reference numeral 20 having a cylindrical barrel 22 that defines an interior surface 21 for containing a fluid (not shown) that includes an open end 25 and a nozzle 26 disposed at the opposite end of the barrel 22. The barrel 22 is formed of a suitable material, such as a plastic. The open end 25 includes an annular flange 31 used to grasp the barrel 22 in order to dispense the fluid contained within the barrel 22. The nozzle 26 opposite the open end 25 includes a tapered portion 27 that extends into a passage 28 extending therethrough that terminates at a dispensing end 29 out of which the fluid flows.

Figure 2:
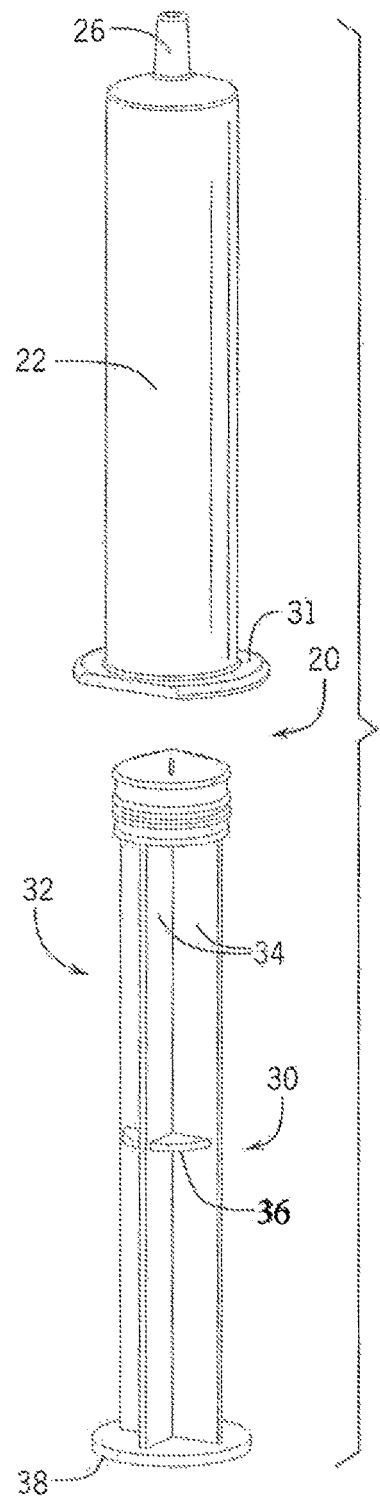
FIG. 2 is an exploded view of the syringe of FIG. 1.

The syringe 20 also includes a plunger 30 that is inserted in the open end 25 of the barrel 22 within the annular flange 31. The plunger 30, in the exemplary non-limiting embodiment shown in FIGS. 1-3 to which reference is now made, includes a body 32 having a rigid structure formed of a suitable material, such as a plastic, with an outer diameter slightly less than that that of the interior 21 of the barrel 22. The body 32 is formed with mutually orthogonal ribs or splines 34 extending the length of the body 32. The splines 34 include supports 35 extending angularly between the splines 34 to provide additional strength to the body 32.

At one end of the body 32 disposed outside of the barrel 22, the plunger 30 includes a push plate 38 that covers one end of the splines 34. The push plate 38 is integral with one end of the splines 34 and is pressed by a user to move the plunger 30 into and through the interior 21 of the barrel 22.

Looking now at FIGS. 5 and 6, in the illustrated exemplary non-limiting embodiment at the inner end 40 of the plunger 30 is disposed a push pin 42. The push pin 42 is formed integrally with the body 32 of the plunger 30, but can also be formed as a separate component attached to the body 32 via threads, adhesives, welding, or other methods, and extends outwardly from the body 32 to terminate at a cap 44 disposed on the pin 42 opposite the body 32. The cap 44 is formed with a lower portion 46 having a diameter larger than the diameter of the push pin 42 in order to function as a stop on the push pin 42. The push pin 42 also includes an upper portion 47 having a tapered or conical shape.

Between the cap 44 of the push pin 42 and the body 32 of the plunger 30 is disposed a seal plate 48. The seal plate 48 is formed of a rigid material and includes a central aperture 50 through which the push pin 42 extends. The aperture 50 has a diameter sufficient to enable the plate 48 to slide along the push pin 42 but small enough to prevent the aperture 50 from passing around the cap 44 or the body 32, such that the seal plate 48 is retained on the push pin 42 between the cap 44 and the body 32. Further, the seal plate 48 has a diameter less than the diameter of the body 32 but greater than the diameter of the cap 44. The seal plate 48 may be formed in the style of a snap or slit washer so that it may be installed on the push pin 42, which itself can be separable from the body 32, or as a solid uniform disk in the case that the push pin 42 is formed as a separate part from the body 32.

Opposite the body 32 the cap 44 is covered by a bung 54. In illustrated exemplary non-limiting embodiment, the bung 54, which is formed of a resilient, flexible material, includes an upper section 56 and a lower section 58. The lower portion 58 is formed with a side wall 60 having a pair of spaced sealing rings 64 located on an outer surface 66 of the side wall 60. The sealing rings 64 in the illustrated exemplary embodiment engage the interior 21 of the barrel 22 to form a fluid seal between the barrel 22 and the bung 54 and are formed as integral protrusions from the side wall 60. Alternatively, the sealing rings 64 can be formed as separate members (not shown) attached in a suitable manner to the side wall 60. The side wall 60 also includes a lower lip 68 located on the side wall 60 opposite the upper section 56 that extends outwardly from the side wall 60 to sealingly engage the interior surface 21 of the barrel 22 separately from the sealing rings 64.

The lower section 58 also defines an interior area 70 within the side wall 60. The interior area 70 is bounded at the lower end by a shoulder 72 that extends inwardly from the side wall 60. The interior area 70 is formed to have a size closely complementary to that of the seal plate 48, such that the shoulder 72 in conjunction with the upper section 56 of the bung 54 effectively holds the seal plate 48 stationary relative to the side wall 60 within the interior area 70. The shoulder 72 also includes a beveled edge 74 at the lower end of the shoulder 72 to facilitate the insertion of the seal plate 48 into the interior area 70. The seal plate 48, in an exemplary, non-limiting embodiment of the invention, has an outer diameter that can be larger or smaller than the internal diameter of the interior area 70, such that the seal plate 48 effectively engages and maintains the sealing engagement of the lower section 58 with the interior 21 of the barrel 21 in both the flexed and relaxed positions for the bung 54 and provides suitable drag force for proper deformation of the bung 54 to tailor the dripless feature for the specific purpose (flow rate requirement, material viscosity, etc.) and syringe barrel 22 size (i.e. smaller cross sectional area syringe requires a lower applied force to generate the same internal pressures of a larger cross sectional area syringe).

Above the seal plate 48, the interior area 70 extends into the upper section 56 of the bung 54. In the illustrated exemplary non-limiting embodiment, the upper section 56 has a conical configuration that tapers inwardly from the side wall 60 to a point 76. The shape of the interior area 70 within the upper section 56 is complementary to the shape of the upper section 46 of the push pin cap 44 to provide a secure engagement of the cap 44 with the upper section 56.

Figure 7:
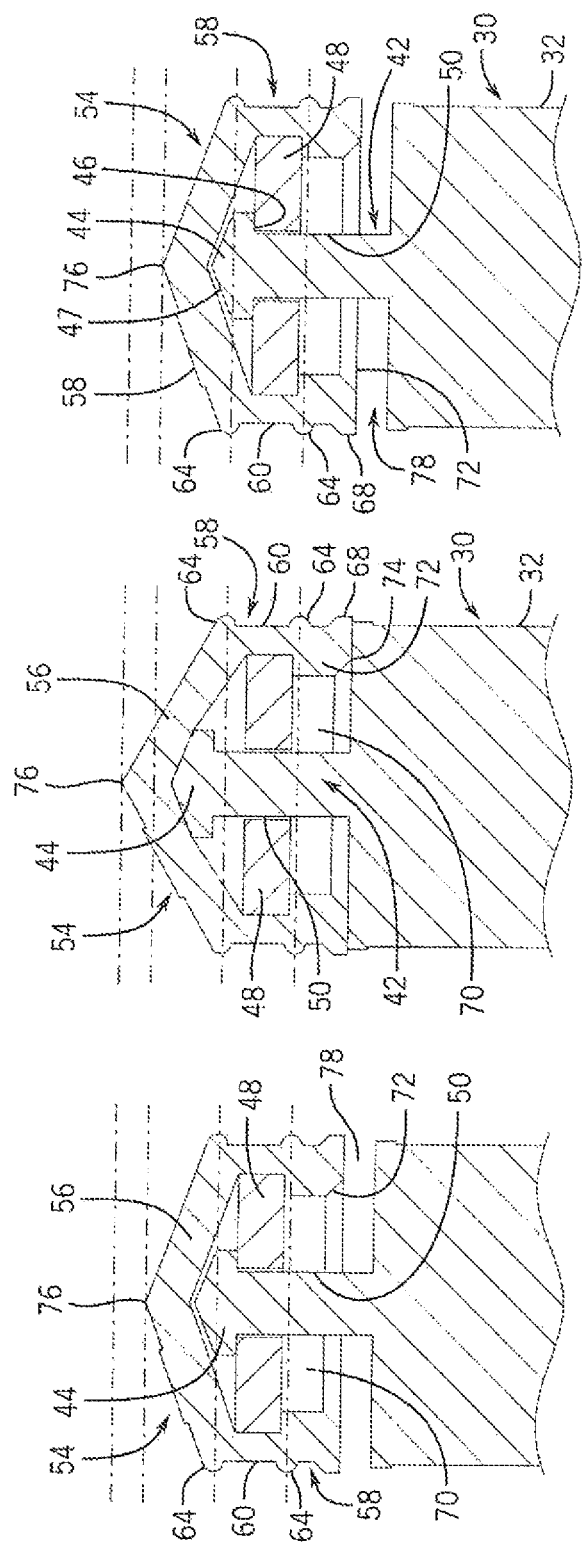
FIGS. 7A-7C are cross-sectional views of the plunger in various operational configurations.

Referring now to FIGS. 7A-7C, in the illustrated exemplary non-limiting embodiment the plunger 30 is shown in a non-dispensing configuration in FIG. 7A. In this configuration, the resiliency of the upper section 56 of the bung 54 conforms to the shape of the cap 44 and holds the seal plate 48 against the cap 44 of the push pin 42, creating a gap or offset 78 between the bung 54 and the body 32 of the plunger 30. In addition, the rigidity of the seal plate 48 presses the side wall 60 of the lower section 58 outwardly to engage the sealing rings 64 with the interior surface 21 of the barrel 22 to maintain the fluid seal between the bung 54 and the barrel 22.

In FIG. 7B, when pressure is applied to the plunger 30 via the push plate 38, the push pin 42 slides through the aperture 50 in the seal plate 48 until the plunger body 32 contacts the bung 54. When contacting the bung 54, the plunger 32 presses the lip 68 outwardly into engagement with the interior 21 of the barrel 22 to provide an additional seal between the bung 54 and the barrel 22 along with the sealing rings 64. In doing so, the offset 78 is removed and the cap 44 presses against the upper section 56 of the bung 54, deforming the upper section 56 outwardly from the remainder of the bung 54. However, even though the upper section 56 is deformed by the push pin 42, due to the placement and rigidity of the seal plate 48, the lower section 58 and the sealing rings 64 thereon remain in secure sealing engagement with the interior surface 21 of the barrel 22. The plunger 30 can continue to be urged or moved forward in this configuration to compress and dispense the fluid from within the barrel 22 through the nozzle 26 while the sealing rings 64 are maintained in sealing engagement with the interior surface 21 of the barrel 22 by the seal plate 48 as the bung 54 slides along the interior surface 21.

Referring now to FIG. 7C, when it is desired to cease the dispensing of the fluid from the barrel 22, the pressure on the plunger 30 is removed. The inherent resiliency of the material forming the bung 54 then acts to retract the upper section 56 of the bung 54 to is unextended configuration. This, in turn, compresses the cap 44 towards the seal plate 48, sliding the push pin 42 through the seal plate 48, and separating the bung 54 from plunger body 32, thereby re-establishing the offset 78. Further, the retraction of the upper section 56 creates negative pressure within the barrel 22 that acts on the fluid remaining in the barrel 22 and nozzle 26, thus drawing this fluid into the barrel 22 and preventing the fluid from dripping out of the nozzle 36. Further, while the upper section 56 is returning to its original unextended configuration, the seal plate 48 remains in secure engagement with the side wall 60 to retain the shape of the lower section 58 while the upper section 56 is deformed, thereby maintaining the sealing engagement of the sealing rings 64 with the interior 21 of the barrel 22 and preventing leakage of the fluid within the barrel 22 from between the barrel 22 and the bung 54.

Referring now to FIGS. 7A-7C, in the illustrated exemplary non-limiting embodiment the plunger 30 is shown in a non-dispensing configuration in FIG. 7A. In this configuration, the resiliency of the upper section 56 of the bung 54 conforms to the shape of the cap 44 and holds the seal plate 48 against the cap 44 of the push pin 42, creating a gap or offset 78 between the bung 54 and the body 32 of the plunger 30. In addition, the rigidity of the seal plate 48 presses the side wall 60 of the lower section 58 outwardly to engage the sealing rings 64 with the interior surface 21 of the barrel 22 to maintain the fluid seal between the bung 54 and the barrel 22.

In FIG. 7B, when pressure is applied to the plunger 30 via the push plate 38, the push pin 42 slides through the aperture 50 in the seal plate 48 until the plunger body 32 contacts the bung 54. When contacting the bung 54, the plunger 32 presses the lip 68 outwardly into engagement with the interior 21 of the barrel 22 to provide an additional seal between the bung 54 and the barrel 22 along with the sealing rings 64. In doing so, the offset 78 is removed and the cap 44 presses against the upper section 56 of the bung 54, deforming the upper section 56 outwardly from the remainder of the bung 54. However, even though the upper section 56 is deformed by the push pin 42, due to the placement and rigidity of the seal plate 48, the lower section 58 and the sealing rings 64 thereon remain in secure sealing engagement with the interior surface 21 of the barrel 22. The plunger 30 can continue to be urged or moved forward in this configuration to compress and dispense the fluid from within the barrel 22 through the nozzle 26 while the sealing rings 64 are maintained in sealing engagement with the interior surface 21 of the barrel 22 by the seal plate 48 as the bung 54 slides along the interior surface 21.

Referring now to FIG. 7C, when it is desired to cease the dispensing of the fluid from the barrel 22, the pressure on the plunger 30 is removed. The inherent resiliency of the material forming the bung 54 then acts to retract the upper section 56 of the bung 54 to is unextended configuration. This, in turn, compresses the cap 44 towards the seal plate 48, sliding the push pin 42 through the seal plate 48, and separating the bung 54 from plunger body 32, thereby re-establishing the offset 78. Further, the retraction of the upper section 56 creates negative pressure within the barrel 22 that acts on the fluid remaining in the barrel 22 and nozzle 26, thus drawing this fluid into the barrel 22 and preventing the fluid from dripping out of the nozzle 36. Further, while the upper section 56 is returning to its original unextended configuration, the seal plate 48 remains in secure engagement with the side wall 60 to retain the shape of the lower section 58 while the upper section 56 is deformed, thereby maintaining the sealing engagement of the sealing rings 64 with the interior 21 of the barrel 22 and preventing leakage of the fluid within the barrel 22 from between the barrel 22 and the bung 54.

Figure 8:
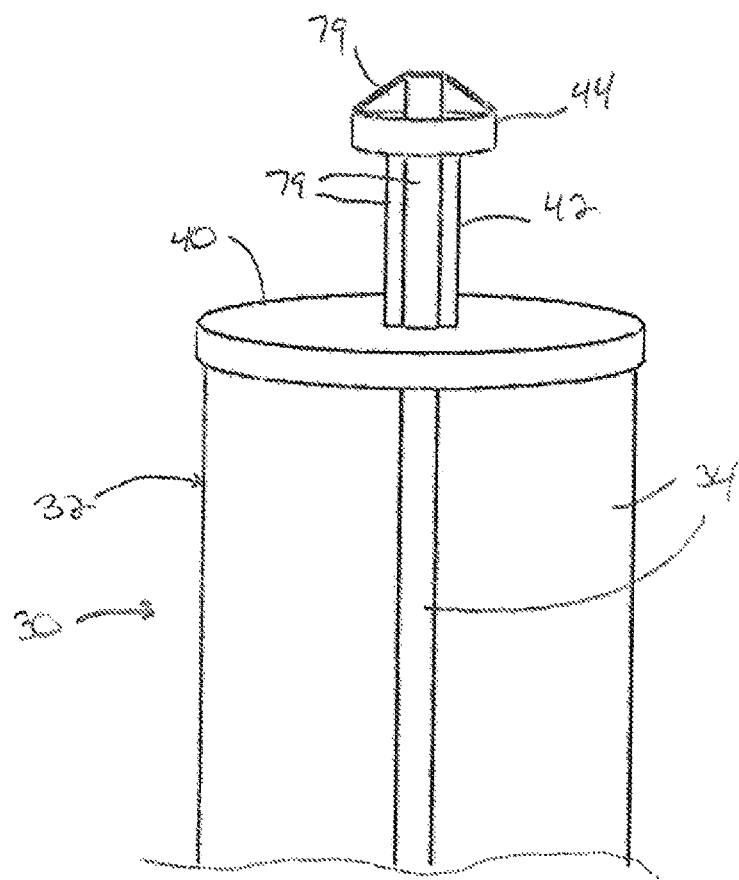
FIG. 8 is an isometric view of one exemplary embodiment of a plunger according to the invention.
Figure 9:
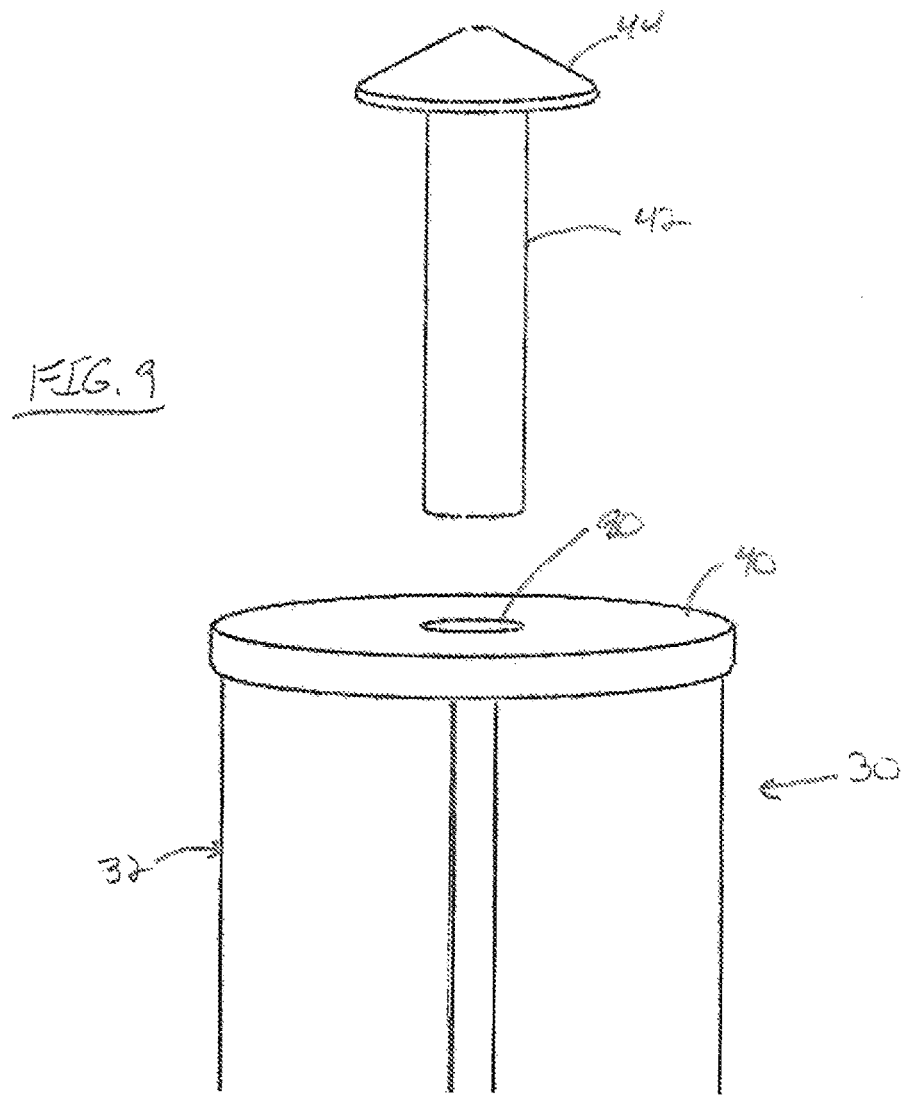
FIG. 9 is an isometric view of one exemplary embodiment of a push pin according to the invention.
Figure 10:
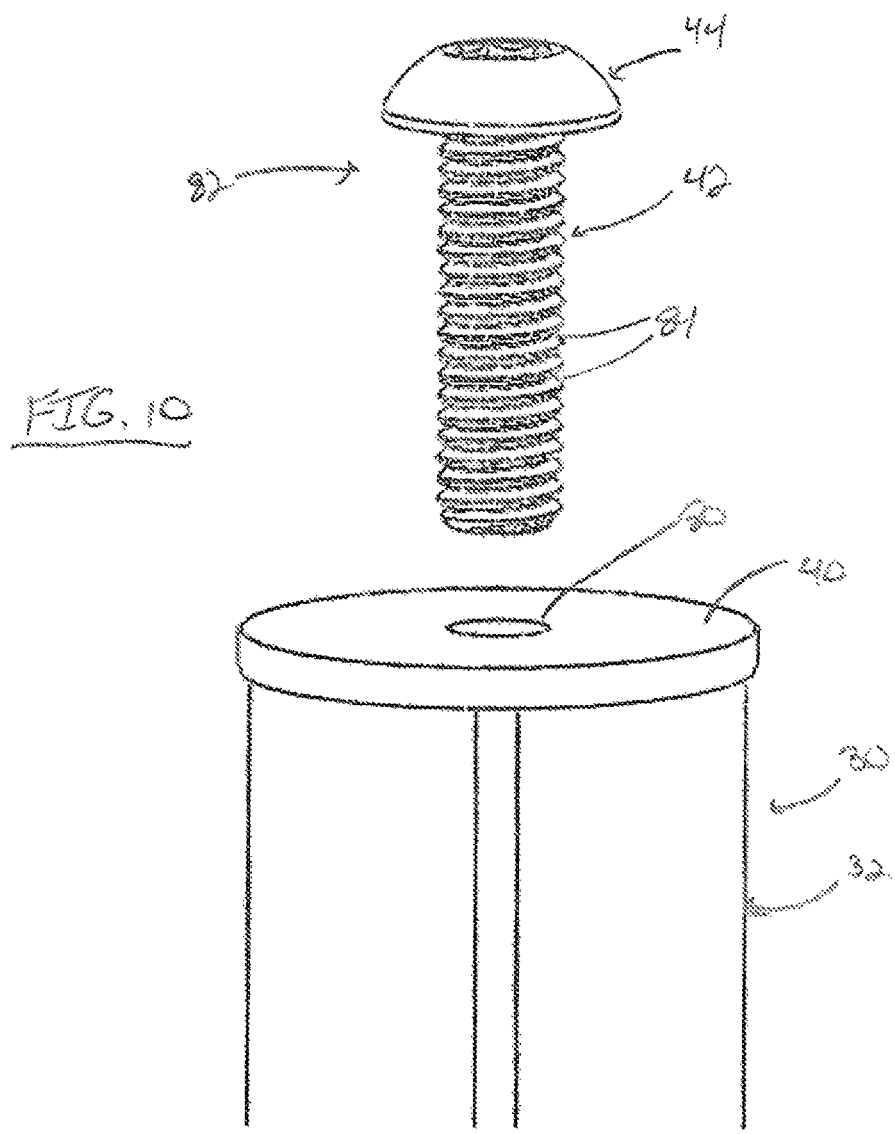
FIG. 10 is an isometric view of another exemplary embodiment of a push pin according to the invention.

In one exemplary embodiment of the invention illustrated in FIG. 8, the push pin 42 and cap 44 are integrally formed with one another and with the plunger 30, such as with splines 79 in the exemplary configuration shown in FIG. 8. Alternatively, the push pin 42 and cap 44 are formed to be removable from the plunger 30. In this embodiment, the pin 42 can be inserted and secured in any suitable manner within a bore 80 formed within the plunger 30 at the inner end 40 of the plunger 30, as illustrated in FIG. 9, such as by an adhesive or a mechanical fastener or structure. The bore 80 can be formed to be smooth or with various friction-enhancing features therein in order to grip and hold the push pin 42 within the bore 80. In other exemplary embodiments, the push pin 42 can be formed to include various friction-enhancing features, such as shown in the exemplary embodiment illustrated in FIG. 10, where the push pin 42 is formed as a screw 82 having exterior threads 84 thereon for engagement within the bore 80.

In other exemplary embodiments of the invention, the sealing ring 48 can be formed as a solid member shown in FIG. 11 including the aperture 50 formed within the ring 48. In this embodiment, the ring 48 can readily be utilized with plungers 30 including push pins 42 that are formed separately from the plungers 30, such as those illustrated in the exemplary embodiments of FIGS. 9 and 10.

Alternatively, to accommodate embodiments of the plunger 30 including push pins 42 that are formed integrally with the plunger 30, as in FIG. 8, or that are already secured to the plunger 30, the seal ring 48 can be formed with a deflection slot 86 that extends from the aperture 50 to the exterior of the seal ring 48. The dimensions of the slot 86 are formed as desired, as shown in the exemplary embodiments of FIGS. 12 and 13, so long as the slot 86 enables portions 88,90 of the seal ring 48 on opposite sides of the slot 86 to be deflected sufficiently to enable the push pin 42 to be moved along the slot 86 into the aperture 50, while being sufficiently rigid to retain the push pin 42 within the aperture 50 during operation of the plunger 30.

In still a further exemplary embodiment of the invention illustrated in FIG. 14, the seal ring 48 is formed with an enlarged aperture 92. The interior 94 of the aperture 92 includes a number of inwardly extending deflection panels 96. The panels 96 are secured to the ring 48 at the periphery of the aperture 92 and terminate adjacent the center 98 of the aperture 92 to define a pin aperture 100. The pin aperture 100 has a diameter less than that of the cap 44, such that the panels 96 can engage and prevent the cap 44 from passing through the pin aperture 100. However, the panels 96 are secured to the ring 48 in a suitable manner, such as a by a living hinge (not shown), that allows the panels 96 to deflect inwardly when the cap 44 and push pin 42 are initially engaged with the ring 48. The panels 96 move away from one another to provide sufficient space for the cap 44 and push pin 42 to pass through the pin aperture 100 until the cap 44 has passes completely through the pin aperture 100. The panels 96 then move back towards their undeflected positions where the panels 96 define the pin aperture 100 with a diameter sufficient to prevent the cap 44 from passing through the pin aperture 100. This exemplary embodiment for the seal ring 48 can be readily utilized with pins 42 an caps 44 that are formed integrally with, or that that are engaged with the plungers 30, among other embodiments.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A syringe comprising:
   a barrel adapted to receive an amount of fluid therein, the barrel defining an open end and a nozzle opposite the open end;
   a plunger disposed at least partially within the open end of the barrel, the plunger comprising a body and a push pin extending from one end of the body that is within the open end of the barrel;
   a bung comprising a compliant and deformable material forming a fluid-tight seal with the barrel, the bung further comprising an upper section formed to be complementary in shape to the cross-section of the barrel forming a fluid-tight seal with the barrel, and a lower section extending outwardly from the upper section;
   a seal plate located under the bung and slidably mounted to the push pin, the seal plate further comprising a central aperture through which the push pin extends, wherein the seal plate comprises a rigid material having a complimentary shape to an interior of the bung lower section and providing support to the interior of the bung lower section; and
   when the bung is deformed outwardly toward the barrel nozzle by the push pin, the bung deforms because of an offset between the bung's lower section and the plunger body with the deformation stopping when the bung bottoms out against the plunger body and returns to an original shape when force is removed from the plunger thereby creating negative pressure within the barrel.

2. The syringe of claim 1 wherein the push pin includes a cap disposed opposite the plunger body, the cap including a lower portion with a diameter greater than the central aperture to function as a stop for the seal plate.

3. The syringe of claim 2 wherein the cap includes an upper portion engaged with the bung.

4. The syringe of claim 3 wherein the upper portion of the cap conforms in shape to the bung.

5. The syringe of claim 1 wherein at least one of the seal plate or the push pin is releasably engaged with the plunger.

6. The syringe of claim 1 further comprising a plurality of sealing rings disposed on the lower section of the bung opposite the seal plate.

7. The syringe of claim 1 wherein the seal plate is stationary relative to the lower section of the bung.

8. A plunger for a syringe, comprising:
   a body and a push pin extending from one end of the body;
   a bung comprising a compliant and deformable material, the bung further comprising an upper section and a lower section, the lower section extending outwardly from the upper section;
   a seal plate located under the bung and slidably mounted to the push pin, the seal plate further comprising a central aperture through which the push pin extends, wherein the seal plate comprises a rigid material having a complimentary shape to an interior of the bung lower section and providing support to the interior of the bung lower section; and when the bung is outwardly deformed by the push pin, the bung deforms because of an offset between the bung's lower section and the plunger body with the deformation stopping when the bung bottoms out against the plunger body and returns to an original shape when force is removed from the plunger.

9. The plunger of claim 8 wherein the seal plate includes a central aperture through which the push pin extends.

10. The plunger of claim 8 wherein the push pin includes a cap located opposite the body to retain the seal plate on the push pin.

11. The plunger of claim 8 wherein the bung's lower section includes a number of sealing rings opposite the seal plate.

12. A method of dispensing a fluid from a syringe, providing a syringe comprising
a barrel adapted to receive an amount of fluid therein, the barrel defining an open end and a nozzle opposite the open end;
a plunger disposed at least partially within the open end of the barrel, the plunger comprising a body and a push pin extending from one end of the body that is within the open end of the barrel;
a bung comprising a compliant and deformable material forming a fluid-tight seal with the barrel, the bung further comprising an upper section formed to be complementary in shape to the cross-section of the barrel forming a fluid-tight seal with the barrel, and a lower section extending outwardly from the upper section;
a seal plate located under the bung and slidably mounted to the push pin, the seal plate further comprising a central aperture through which the push pin extends,
wherein the seal plate comprises a rigid material having a complimentary shape to an interior of the bung lower section and providing support to the interior of the bung lower section; and
when the bung is deformed outwardly toward the barrel nozzle by the push pin, the bung deforms because of an offset between the bung's lower section and the plunger body with the deformation stopping when the bung bottoms out against the plunger body and returns to an original shape when force is removed from the plunger thereby creating negative pressure within the barrel;
applying a force to the plunger to press the push pin through the seal plate and against the bung to dispense the fluid from the nozzle; and
removing the force on the plunger to cease dispensing the fluid from the nozzle.

13. The method of claim 12 wherein the step of applying the force to the plunger comprises urging the push pin into the bung to expand the upper section of the bung.

14. The method of claim 13 wherein the step of urging the push pin into the bung comprises sliding the push pin through a central aperture in the seal plate.

15. The method of claim 12 wherein the step of removing the force to the plunger comprises withdrawing the push pin from the bung to contract the upper section of the bung and apply a negative pressure to the fluid within the nozzle.

* * * * *